United States Patent [19]

Buschmann et al.

[11] 3,965,195

[45] June 22, 1976

[54] PROCESS FOR THE PRODUCTION OF FORMALDEHYDE

[75] Inventors: Karl Buschmann, Neustadt; Hans Diem, Mannheim; Guenther Matthias; Friedrich Wodtcke, both of Ludwigshafen, all of Germany

[73] Assignee: Badische Anilin- & Soda-Fabrik Aktiengesellschaft, Ludwigshafen (Rhine), Germany

[22] Filed: Apr. 23, 1975

[21] Appl. No.: 570,801

Related U.S. Application Data

[63] Continuation of Ser. No. 321,549, Jan. 5, 1973, Pat. No. 3,870,740.

[30] Foreign Application Priority Data

Jan. 13, 1972 Germany............................ 2201434

[52] U.S. Cl. .......................................... 260/603 HF
[51] Int. Cl.² ....................................... C07C 45/16
[58] Field of Search ............... 260/603 HX; 321/549

[56] References Cited
UNITED STATES PATENTS 3,318,955 3/1967 Gerloff........................ 260/630 Q X
3,728,398 4/1973 Maux............................. 260/603 HF

OTHER PUBLICATIONS

Ross, "The Inhibition of Foaming," Rensselar Polytechnic Institute (1970) Troy.

Ross "Chem. Abstract, " vol. 67, p. 12856, (1967).

Primary Examiner—James O. Thomas, Jr.
Assistant Examiner—W. B. Lone
Attorney, Agent, or Firm—Johnston, Keil, Thompson & Shurtleff

[57] ABSTRACT

Production of formaldehyde by vaporization of a mixture of methanol and water in the presence of a mixture of alkanols and dialkylethers, and then by a catalytic, oxidizing dehydrogenation of methanol. The formaldehyde obtainable according to the process of the invention is useful as a disinfectant, a tanning material, a reducing agent or as a valuable initial material for the production of synthetic resins, adhesives and plastics.

10 Claims, No Drawings

PROCESS FOR THE PRODUCTION OF FORMALDEHYDE

This is a continuation of application Ser. No. 321,549, filed Jan. 5, 1973, now U.S. Pat. No. 3,870,740.

The invention relates to a process for the production of formaldehyde by vaporization of a mixture of methanol and water in the presence of a mixture of alkanols and dialkylethers after which the methanol is subjected to a catalytic, oxidizing dehydrogenation.

It is known from Ullmanns Encyklodaedie der technischen Chemie, Vol. 7 (1956), pages 659 ff, that a methanol in the form of an aqueous solution, e.g. a 55% methanol solution, can be vaporized in a vaporizer, the vaporous mixture mixed with air and a methanol then subjected to an oxidizing dehydrogenation on a silver or metal oxide catalyst. There is used condensation water or also a chlorine-free and preferably softened industrial water. Such industrial waters include ground water, well water, surface water such as river water, drinking water, boiler feed water and occassionally also sea water. According to its origin and preparation, the water being used can contain many substances as impurities, e.g. metal salts such as iron chloride, alkaline earth compounds as common in water hardening, alkali salts, metals such as zinc, aluminum or copper as obtained, for example, from raw materials, nitrates, nitrites, phosphates and organic decomposition products such as phenols. As the initial reactant, one can use crude methanol or a pure methanol which is recovered from the crude methanol by fractional distillation. Crude methanol can vary in its composition according to the process of its production (Ullmanns Encyklopaedie der technischen Chemie, Vol. 12, pages 398 ff), and such crude methanols generally contain about 95 to 70% by wt. methanol, 1 to 29% by wt. of water and 0.1 to 6% by wt. impurities. As impurities one can mention, for example, alkali compounds such as sodium formate, sodium hydrogen carbonate, sodium carbonate, sodium acetate, sodium sulfide, sodium methylate, potassium hydroxide, sodium hydroxide; formic acid; aldehydes such as acrolein, glyoxal, propionaldehyde and acetaldehyde; ketones such as acetone and butanone-2; glycol; hexane; dimethylether; organic or inorganic compounds, e.g. formates or sulfides of metals such as iron, chromium, copper, aluminum, zinc and magnesium; sulfur compounds such as dimethylsulfide; esters such as dimethylterephthalate; amines such as monomethylamine, dimethylamine and trimethylamine; and ammonia. As a rule, alkaline impurities are especially present because the acids found in methanol are neutralized with alkali in practically all synthesis procedures. All these impurities occur according to the process for producing the methanol or its storage and may be present in different amounts and/or numbers of components.

In the vaporization of such mixtures of methanol and water, difficulties frequently occur to a considerable degree. For example, the speed of vaporization decreases, the vaporizer sump retains liquid and large amounts of foam with relatively large individual bubbles and a relatively stable consistency occur at the surfaces of the vaporizing methanol solution. Simultaneously, the pressure in the vaporizer can increase and the liquid under admixture with air can form a thick foam layer to an increasing extent over a period of time. In many a case, the foam is carried over, collects on the catalyst and disturbs or hinders the reaction of the methanol. Specifically, in large technical operations, in which there is usually vaporized about 1000 to 20,000 kilograms of methanol solution per hour from a 60 to 95% by wt. methanol solution. After 1 to 16 hours, frequently at intervals of 1 to 3 hours, the pressure can rise from the usual 1.2 atmospheres up to 1.5 to 1.8 atmospheres if a 2-plate vaporizing column is used. At the same time, the amount of vaporized solution is reduced each hour to 70 to 80% of its original value.

All these difficulties lead to the worst kind of operational disturbances or stoppages. At the very least, interruptions of the operation are necessary with reference to the feed of materials and the supply of heat. These disturbances can be reduced through suitable construction of the vaporizer only in certain cases. Even then prior carefully constructed vaporizers have exhibited after long operation the disturbances of the above-mentioned kind whose causes are frequently unknown and cannot be attributed solely to the construction of the vaporizer. The cause of these difficulties resides for the most part in the type and amount of impurities present in the mixture, the effect of these impurities being generally unforeseeable in individual cases. A certain alkali content especially appears to promote the foaming effect. Also, an increase of the alkali content or a change of the operation from crude methanol to a pure methanol as initial material can cause disturbances. German Pat. No. 1,618,438 teaches on page 2, first paragraph, that alkalis promote the formation of foam in this process and underscores the importance of the use of an especially pure methanol. Once a foam layer is formed, it is very difficult to remove and also the cleaning of the vaporizer gives rise to a renewed foaming in the cleaning water.

In various industries, for example in the production of paper, textile dying or textile printing, antifoaming agents have been considered for use in various aqueous treating baths, for example wash baths, mercerizing liquors, etc. The antifoaming agents do not eliminate these difficulties, at least not in a sufficient measure. Antifoamers or other auxiliaries have not been previously described for the above-mentioned difficulties in methanol/water mixtures being used in connection with the production of formaldehyde. Besides, such an auxiliary must also fulfill conditions for which many antifoamers are unsuitable. The volatility with steam or methanol-steam mixtures should be slight. The auxiliary must be stable in the presence of alkali so that it is not decomposed during its residence in the vaporizer and thus retains its effect, thereby excluding esters and acids. The auxiliary must be heavier than the sump discharge or sufficiently soluble therein so that it does not become concentrated in the vaporizer, as is the case for example with silicon oils. It must be effective in such small amounts that it does not disturb further processing if it accrues partly in the final product.

Also, the effectiveness of a substance in a specific case cannot be generally determined from its properties as an antifoaming agent. A large number of parameters play a roll in the formation of foam, for example viscosity, surface tension and differences of surface tensions in a bubble and on the surface of a solution. Pure liquids do not give a stable foam. See K. Edelmann, Lehrbuch der Kolloidchemie, Vol. 1, pages 309 to 310 (VED, Berlin 1961), and H. Freundlich, Kapillarchemie, pages 1091 to 1093 (Leipzig 1922). The kind and amount of an antifoamer suitable for a specific case cannot be derived from other known cases, and also the foaming effect of a substance or an impurity in a given medium is not foreseeable. See Ross, The Inhibition of Foaming, pages II, 17, 21 and 29 (Rensselaer Polytechnic Institute, N.Y. 1950); and Bikerman, Foams Theory and Applications, pages 74 and 297 (Reinhod Publ. Corp. 1953).

It is an object of this invention to provide a process in which formaldehyde can be produced in a simpler and more economical manner. It is also an object of the invention to produce formaldehyde in good theoretical yields, better space-time yields and in high purity.

It has now been found, in accordance with the invention, that one can advantageously obtain formaldehyde by the vaporization of a mixture of methanol and water and then subjecting the vaporous methanol to an oxidizing dehydrogenation in the presence of a catalyst if the vaporization is carried out in the presence of a solvent mixture of at least one alkanol of more than 7 carbon atoms and at least one dialkylether of more than 7 carbon atoms in each alkyl group.

With reference to the state of the art, the process of the invention surprisingly provides a simpler and more economical method of obtaining formaldehyde in good yields, higher space-time yields and better purity. The above-noted difficulties and operational disturbances are avoided. The yield of formaldehyde per unit time and therewith the continuous vaporization velocity of the methanol solution generally amounts to about 1.5 to 2.5 times that of the usual operation which is susceptible to disturbances. These advantageous results were not to be expected with the solvent mixture of alkanols and ethers as prescribed by the invention, particularly where it was known (German Pat. No. 1,618,438) that ethers such as dimethylether and alkanols such as isobutyl alcohol disturb the production of formaldehyde.

As the initial materials for the process, it is suitable to use pure methanol or technical methanol in admixture with water. The concentration of this initial aqueous mixture can suitably vary between 50 and 95% by wt., preferably between 58 and 70% by wt. There can also be used a crude methanol which as a rule is purified according to the processes described in German Pat. No. 1,277,834, No. 1,235,881 and No. 1,136,138 by separation of a lower boiling fraction or by treatment with oxidizing agents and/or alkaline agents.

The pure or crude methanol can be obtained according to known processes (Ullmann, loc. cit., Vol. 12, pages 402 ff), especially by high pressure processes. More recently, methanol has also been produced according to the so-called low pressure process. In this process, carbon monoxide and hydrogen are converted to methanol at pressures below 150 atmospheres and at temperatures below 350°C. As catalysts for this low pressure process there can be used those with a content of copper, zinc and a third element, e.g. chromium, or a very difficultly reducible metal of Groups II or IV of the periodic system of elements. Such catalysts have been described for example in British Pat. Nos. 1.010,871 and 1,159,035. The crude or purified methanol of this low pressure process can also be used in the process of the invention. The vaporization is carried out discontinuously or advantageously in a continuous manner, as a rule in one of the known vaporizing units (Ullmann. loc. cit., B.I.O.S. Final Report No. 1,331; F.I.A.T. Final Report No. 999) at a temperature of the vaporizing liquid of the uppermost vaporization plate of 68°C. to 100°C., preferably about 68°C. to 88°C., without pressure or under pressure, suitably under a pressure of 1.0 to 1.8 atmospheres.

There is added to the aqueous methanol solution a solvent mixture of at least one alkanol of more than 7 carbon atoms, preferably 8 to 24 and especially 8 to 12 carbon atoms, and at least one dialkylether wherein each alkyl group contains more than 7 carbon atoms, preferably 8 to 24 and especially 8 to 12 carbon atoms. The dialkylethers can suitably contain the same alkyl groups and/or different alkyl groups than those of the alkanols. The alkyl groups can have a branched chain or preferably a straight chain. In general, one uses the solvent mixture in an amount of 0.0001 to 0.8 and preferably 0.0005 to 0.1% by wt. with reference to the methanol (calculated as 100%). Mixtures of 1 to 5 alkanols and 1 to 5 dialkylethers are especially useful, particularly wherein the number of alkanol components is advantageously greater than the number of dialkylether components. The total amount of the alkanol content is about 50 to 900, preferably 100 to 400% by wt. with reference to the total amount of the ether.

Mixtures of 2 to 5 alkanols and 1 to 3 dialkylethers are especially preferred wherein the two alkyl groups of the ether and the alkyl group of one of the used alkanols are the same. For example, one can mention the octyl-, nonyl-, decyl-, undecyl-, lauryl-, tridecyl-, myristyl-, pentadecyl-, cetyl-, heptadecyl-, stearyl-, nonadecyl-, aracyl-, heneicosyl-, behenyl-alcohols and their corresponding ethers. Such mixtures are obtained, for example, in the distillation of fatty alcohols which are produced according to various processes (Ullmann, loc. cit., Vol. 7, pages 440 ff), suitably according to an oxo synthesis. Especially useful are fractions of such a fatty alcohol distillation with a boiling point at 760 mm Hg of 80° to 280°C., preferably 145° to 250°C. and especially 150° to 210°C. Such fatty alcohol fractions, which are sometimes identified as "thick oils", generally have refractive indices $n_D^{20}$ of 1.425 to 1.451 and densities $d_4^{20}$ of 0.76 to 0.79. The mixture preferably has a saponification number under 20 and an acid number under 1. Some unsaturated fatty alcohols or the corresponding ethers may be present, the iodine number of the mixture preferably falling below 2. The above-cited fatty alcohol fractions (thick oils) are preferably used in an amount of about 0.0001 to 0.8, preferably 0.0005 to 0.1 and especially 0.002 to 0.01% by wt. with reference to the methanol (calculated as 100%). The thick oils can also contain admixed therewith up to 5% by wt. of an ester, e.g. acetic acid nonyl ester, and up to 0.5% by wt. of water.

The vaporization can be carried out in the following manner. One vaporizes a methanol-containing aqueous formaldehyde solution to which there has been added said solvent mixture, especially a so-called "thick oil", at the previously mentioned temperature. One can employ directly or indirectly heated vaporizers or similar evaporators: for example, a tubular vaporizer, Robert vaporizer, Kestner vaporizer, forced circulation vaporizer, multi-stage vaporizers; or rectification columns, e.g. a sieve plate-, Oldershaw-, glass plate-, bell plate- or valve plate-column. There are preferably used vaporization velocities of 1000 to -b 20,000 kilograms per hour of aqueous methanol solution having a content to 58 to 70% by wt. methanol.

In a continuous operation, the methanol solution can be conducted to the vaporizer sump, to the upper third of the vaporizer or preferably to the uppermost plate of the vaporizer. The solvent mixture employed as the additive, i.e. such as the "thick oil", can be introduced preferably together with the methanol solution or also separately therefrom. A separate feed conduit can be located at optional points in the vaporizer, preferably being located above the uppermost plate, for example, 20 to 50 cm above the uppermost sieve plate. The solvent mixture can be added continuously or discontinuously. With discontinuous dosing of the solvent mixture, it is sufficient for the most part to add it at intervals of 1 to 25 hours in amounts corresponding to the selected time period.

The so-called "thick oils" or equivalent mixtures of fatty alcohols and their corresponding ethers, e.g. as formed with alkyl groups of 8 to 24 and especially 8 to 12 carbon atoms, have a relatively high viscosity. In view of this viscosity and the slight amount required, the thick oil is preferably first dissolved or suspended in a suitable liquid solvent, e.g. methanol or an aqueous methanol solution. Typical examples of the solubility of the thick oil are given in the following table:

| Solvent | Solubility (grams "thick oil" in 100 grams solvent) |
|---|---|
| (1) methanol | unlimited miscibility |
| (2) 60% by wt. methanol 40% by wt. water | 0.5 |

Thus, while the thick oil or equivalent mixtures of alkanols and dialkylethers have very poor solubility in water, they can be easily dissolved in methanol or else suspended in a methanol/water mixture.

Likewise, one can introduce methanol and water separately from each other discontinuously or preferably continuously and the solvent mixture, preferably the thick oil, is added continuously or discontinuously to one or the other components of the aqueous methanol mixture. In order to avoid interruption of the boiling of the vaporizer sump in feeding components thereto, one preferably brings the added components or a prior mixture thereof to a temperature close to the temperature of the sump.

The methanol-water-vapor mixture leaving the vaporizer is advantageously conducted in admixture with the recycled off-gas and suitably with an inert gas to the reaction zone. As an inert gas, one can use nitrogen, for example, in the process of the invention. Preferably the vapor mixture is simultaneously mixed with the oxidizing agent and with the off-gas and/or inert gas.

As the oxidizing agent there can be used pure oxygen as well as gases containing free oxygen, especially air. Oxygen and methanol are utilized preferably in the molar ratio of 0.3 to 0.6, especially 0.4 to 0.5 mols of oxygen for each mol of methanol. Methanol and air are preferably employed in the molar ratio of 1 mol of methanol for each 1.4 to 2.9 mols of air. The oxidation may also be accomplished in the presence of 1 to 2, advantageously 1 to 1.65 mols and especially 1.3 to 1.5 mols of off-gas for each mol of methanol.

Any number of suitable silver catalysts can be used for the process according to the invention, for example, the catalysts described in German Pat. No. 1,231,229 and Ullmanns Encyklopaedie, Vol. 7, pages 659 ff. One preferably uses a 2-layer silver catalyst as set forth in German Pat. No. 1,294,360 and in the German Specification No. 1,903,197.1. For the production of the catalysts and carrying out the corresponding reaction with these catalysts, reference is made to the prior art generally as well as to the cited publications.

A preferred embodiment of the process according to the invention resides in carrying out the reaction by passing the vaporous reactants downwardly through a 2-layer silver catalyst bed wherein the lower layer has a depth of 50 to 40 mm, especially 20 to 30 mm and consists of at least 50% by wt. of crystals whose particle size is 1 to 4 mm, preferably 1 to 2.5 mm and wherein the upper layer has a depth of 4.75 to 3 mm, especially 1 to 2 mm, and consists of crystals with a particle size of 0.1 to 1 mm, especially 0.2 to 0.75 mm. This catalyst is loaded with 1 to 3 metric tons, especially 1.4 to 2.4 metric tons of methanol per square meter of catalyst cross-section per hour. For large scale operations, one preferably uses a catalyst bed with a diameter of at least 0.5 and preferably 1 to 3 meters.

The oxidation is otherwise carried out in a known manner, for example, wherein one leads a gas mixture of methanol vapor, water vapor, air, an inert gas if desired and preferably off-gas in the above-mentioned amounts through the silver catalyst at temperatures of about 550° to 750°C., expecially 600° to 700°C.

The process is generally continuously carried out between pressures of 0.5 and 2 atmospheres, preferably between 0.8 and 1.8 atmospheres. It is preferable in this process to cool the reaction gases leaving the catalyst zone within a short period of time, for example, in less than 1/10 seconds, to a substantially lower temperature of 350°C. The cooled gas mixture is then suitably conducted into an absorption column in which the formaldehyde is washed out of the gas mixture with water, preferably in a counter-current stream of the wash water.

One part of the remaining off-gas, i.e. after washing out formaldehyde, is permitted to escape while the remaining part is conducted back advantageously into the recycle for the reaction. That portion of the off-gas which is conducted back to the reaction amounts to about 1 to 2 mols for each mol of methanol being fed into the reaction. The off-gas consists essentially of nitrogen, hydrogen, carbon dioxide, carbon monoxide, water, methanol, argon and usually about 0.1 to 0.5 grams of formaldehyde in 1 cubic meter of off-gas. The off-gas is suitably treated with an oxidizing agent and/or a basic compound, advantageously in an amount such that a pH of at least 10 and preferably 11 to 13.5 is achieved. The off-gas is then mixed with the remaining components of the initial mixture of the reaction and then conducted again to the reaction zone. As basic compounds, there are preferably employed alkaline compounds, either in solid form or dissolved in water, such as hydroxides, oxides or carbonates of alkaline or alkaline earth metals or other alkaline reacting substances, for example, alkali metal alcoholates or strongly basic and generally high-boiling amines such as triethanolamine. As oxidizing agents, there can be used by way of example: hydrogen peroxide or sodium peroxide in aqueous solution; perborates or percarbonates preferably in admixture with water; potassium permanganate; or chromic acid and preferably in the form of an aqueous 0.5 to 10% by wt. solution. In general, there are used 0.02 to 10 grams of oxidizing agent for each 1 cubic meter of off-gas. This treatment is usually continuously carried out at a temperature of between 20° and 150°C. at normal pressure or at an elevated pressure. Also, a two-stage treatment with both components is possible, preferably first with the basic compound and then with the oxidizing agent. The treatment of the off-gas is preferably carried out in accordance with United States patent application Ser. No. 141,002, filed May 6, 1971.

In the case of using a silver catalyst, one can also coemploy an amine according to the process described in the pending United States application Ser. No. 236,210, filed Mar. 20, 1972. In general, the amines used with the silver catalyst are secondary or tertiary amines employed in an amount of 0.00003 to 0.0005 mols per mol of methanol. These amines may be used in pure form or in solution, i.e. in suitable solvents such as water, alkanols including ethanol or preferably methanol or appropriate mixtures of such solvents. Generally solutions of 20 to 60% by wt. of amine are used. Mixtures of amines may also be used. The temperature of the amine or the amine solution is advantageously between 20° and 80°C. The amine can be supplied to the starting mixture in the vaporizer into which the added water is metered or else the amine can be introduced into the vaporizer together with the methanol. It is convenient to pump the amine or the amine solution onto the boiling liquid in the vaporizer or into the vaporizing liquid in circulation.

When using metal oxides as the catalyst, the known reaction is carried out under appropriate conditions (Ullmann, loc. cit., as well as the processes generally taught by the prior art), but generally without the above-mentioned recycle of off-gas in such cases. The preferred catalysts are oxides of iron and molybdenum, without a carrier material or preferably on a carrier, for example, according to the processes described in the following United States applications:

Ser. No. 48,444, filed June 22, 1970; and
Ser. No. 118,609, filed Oct. 12, 1971.

One uses by way of example in a preferred embodiment of these catalytic processes an amount of 5 to 15% and preferably 5 to 10% by wt. of methanol with reference to the amount by weight of air. In continuous operation, one advantageously reacts in the presence of the catalyst at least 0.1 to 1 kg, preferably 0.2 to 0.7 kg of methanol per hour per liter of catalyst.

The catalyst may contain from 3 to 20, preferably from 4 to 15% by wt. of the oxide of iron and molybdenum, taken with reference to a carrier, preferably a silicate carrier. As a rule, the oxide is selected in a proportion of 1 part by weight of $Fe_2O_3$ to 3 to 12 parts by weight of $MoO_3$, preferably 1 part by weight $Fe_2O_3$ to 5 to 7 parts by weight $MoO_3$. In addition, there may also be present in the catalyst one or more other additives such as the oxides, phosphorous tri- and pentoxides of cobalt, nickel, chromium, tungsten or aluminum in an amount of 0.5 to 5%, preferably 0.5 to 3% by wt., with reference to the carrier, or in an amount of 0.1 to 2% by wt. with reference to the total amount of oxide when there is no carrier.

As silicate carriers there are generally used alkali and alkaline earth metal silicates, especially the silicates of calcium, magnesium, zinc, cerium, zircon, aluminum or their mixtures. The silicates may also be in the form of aluminosilicates, borosilicates or zeolites and calcined magnesium silicates are preferred. They may suitably contain additives such as alkali sulfate or oxide, e.g. fused silicates or so-called glasses of soda, sulfate, potassium, potassium sulfate and the like. Mixtures of various cations with silicates are also suitable, e.g. in the form of silicates in the nature of olivine, phenacite, titanite, chrysolite, benitoite, axinite, cordierite, milarite, steatite, orthoclase, plagioclase or albite.

However, other carrier materials may also be used, for example quartz, argillaceous earth, silicon carbide, porcelain, magnesium oxide or rutile ($TiO_2$). Fused aluminum oxide is also quite suitable. Especially useful carriers are those which have an internal surface area between 9 and 5 m²/g. They can be used in the form of granules, pellets, rings and advantageously as spheres with a diameter of 3 to 12 millimeters.

The catalyst thus consists of particles of any shape but preferably in the form of spheres or balls, with a diameter of about 4 to 12, preferably 6 to 10 mm and a surface area of below 10, preferably about 0.01 to 5 m² per gram of catalyst. In general, it is preferable to use a spherical silicate carrier which has been treated with an aqueous solution of iron and molybdenum salts. Preferred are those catalyst preparations described in the above-mentioned patent specifications, e.g. in application Ser. No. 188,609.

The oxidation of the methanol with the use of the above-noted oxide catalysts is usually carried out at temperatures between 280° and 420°C., preferably between 320° and 370°C. at normal or superatmospheric pressure and either discontinuously or preferably continuously. The reaction can be initiated as follows. A reactor is filled with the catalyst produced in the above-noted manner. As the reactor, it is advantageous to use a tubular reactor with outer cooling and any suitable number of tubes, e.g. up to about 15,000 which are preferably free of inserts such as heating cores, shafts, cells or the like. In a preferred construction, the inner diameter of the tubes is at least 25 mm, especially 30 to 34 mm, and the length of the tubes is about 0.5 to 5 meters. After the reaction, the reaction mixture is generally worked up in the same manner as that described above in connection with the use of silver catalysts and the formaldehyde is recovered by absorption.

The formaldehyde produced by the process of the invention is a disinfectant, tanning material, reducing agent and valuable initial material for the production of synthetic resins, adhesives and plastics. Reference is made to Vol. 7 of Ullmann's Encyklopaedie, page 670, for the many uses of formaldehyde.

The following examples further illustrate the invention wherein parts are parts by weight.

EXAMPLE 1

In a vaporizer column having three sieve plates, a mixture of 40 parts crude methanol (24 parts methanol, calculated as 100%, 0.16 parts alkali and 16 parts water) are vaporized hourly and mixed per hour with 71 parts air with the resulting vapor/air-mixture being reacted on a silver catalyst (250 parts) at 1.2 atmospheres and 680°C. The silver catalyst consists of a lower 20 mm thick layer of silver with a particle size of 1.5 to 3 mm and an upper 1 mm thick layer of silver with a particle size of 0.2 to 1 mm. The vapors are directed downwardly through the two catalyst layers. The throughput or space velocity amounts to 1.9 metric tons of methanol per square meter of catalyst bed cross-section per hour. The reaction mixture is cooled to 150°C. and dissolved in 5.2 parts of water per hour in a washing tower.

The vaporizer contains a constant amount of about 60 parts liquid. After three hours of operating time, a strong formation of foam begins. 10 hours after the beginning of the reaction, the foam layer is 210 cm high and covers all three vaporizer plates. The liquid level indicator shows an apparent fluctuation of the liquid level of ± 100 cm. An addition of 0.5 parts of a 50% by wt. caustic soda solution does not reduce the formation of foam. Then, within about 2 minutes, there are added 0.0005 parts of "thick oil" dissolved in one part of a mixture of 60% by wt. crude methanol and 40% by wt. water, this "thick oil" consisting of 60% by wt. nonylalcohol, 10% by wt. octylalcohol, 5% by wt. decylalcohol, 3% by wt. dodecylalcohol, 2% by wt. myristylalcohol and 10% by wt. dinonylether as well as 10% by wt. dioctylether. Immediately after this addition the foam disappears completely, the vaporizer plates remain free and the liquid boils quietly. Fluctuations of the liquid level are no longer determinable. After this single small addition of the thick oil, the foam no longer appears over a period of 10 days up to the time when the unit is closed down. The discharge or output prior to the addition of the thick oil was on the average 14.0 parts per hour of formaldehyde, but after the addition of the thick oil it averaged 19.7 parts of formaldehyde per hour.

EXAMPLE 2

Into a vaporizer column with three sieve plates, there is introduced 61 parts per hour of a mixture of 40% by wt. water and 60% by wt. crude methanol. This mixture is vaporized at 1.4 atmospheres and 74°C. and then reacted in the same manner as Example 1. The introduced mixture contains 0.08% by wt. of sodium hydroxide. A 2 cm thick foam layer forms on the upper plate while a 30 cm thick layer forms on the bottom plate. Analogous to Example 1, there can be observed all of the same disturbances of the speed of vaporization and delay of boiling.

Then within a period of 10 minutes, there are added 0.2 parts of a 60% by wt. aqueous methanol solution and 0.0006 parts of a thick oil (consisting of 50% by wt. nonylalcohol, 5% by wt. octylalcohol, 5% by wt. laurylalcohol, 20% by wt. dinonylether, 18% by wt. dioctylether, 0.2% by wt. water and 1.8% by wt. of acetic acid nonyl ester). The foam breaks down immediately after this addition. The initial mixture then vaporizes without interruption and the unit remain free of foam until it is closed down (2 days after the addition). The yield prior to the thick oil addition amounted to 22 parts of formaldehyde per hour, but after this addition the yield was 30.0 parts of formaldehyde per hour.

EXAMPLE 3

In a preparation carried out analogously to Example 2, there is continuously introduced with the initial materials per hour an amount of 0.0003 parts of a thick oil consisting of 70% by wt. decylalcohol, 10% by wt. octylalcohol, 8% by wt. dodecylalcohol, 10% by wt. didecylether and 2% by wt. acetic acid decyl ester. The vaporization takes place without any disturbance or interruption. The unit remain free of foam until it is shut down (60 days). The output amounts to 29.9 parts of formaldehyde per hour.

From these and other examples, it has become evident that an improved production of formaldehyde is achieved with the "thick oil" being added in only very small amounts sufficient to prevent or inhibit foaming in the vaporizer. Moreover, there is no subsequent disturbance of reduction in yields of the formaldehyde when using any of the conventional catalysts for the oxidizing dehydrogenation of the methanol reactant. To the contrary, the yields in terms of an hourly output of formaldehyde are markedly increased.

The invention is hereby claimed as follows:

1. In a process for the production of formaldehyde by vaporization of a mixture of methanol and water and then subjecting the methanol in the vapor phase to an oxidizing dehydrogenation in the presence of a catalyst at elevated temperature of from about 550° to 750°C and at a pressure of from 0.5 to 2 atmospheres where a silver catalyst is employed and at a temperature of from about 280° to 420°C where an oxide catalyst is employed, the improvement which comprises carrying out said vaporization in the presence of a solvent mixture of at least one alkanol of from 8 to 24 carbon atoms and at least one dialkylether of from 8 to 24 carbon atoms in each alkyl group, the amount of said solvent mixture being from 0.0001 to 0.8% by weight with reference to said methanol, the amount of said alkanol in this mixture being from 50 to 900% by weight based on the weight of said dialkylether.

2. A process as claimed in claim 1 wherein the vaporization is carried out with an aqueous mixture of between 50 and 95% by weight methanol.

3. A process as claimed in claim 1 wherein the vaporization is carried out at a temperature of the vaporizing liquid at the uppermost plate of the vaporizer of 68°C. to 100°C. and under a pressure of 1.0 to 1.8 atmospheres.

4. A process as claimed in claim 1 wherein said at least one alkanol has 8 to 12 carbon atoms and said at least one dialkylether has 8 to 12 carbon atoms in each alkyl group.

5. A process as claimed in claim 1 wherein said solvent mixture is present in an amount of about 0.0005 to 0.1% by weight with reference to the methanol (calculated as 100%).

6. A process as claimed in claim 1 wherein said solvent mixture consists of 1 to 5 alkanols and 1 to 5 dialkylethers with a total amount of 50 to 900% by weight of the alkanol portion with reference to the total amount of the dialkylether portion.

7. A process as claimed in claim 1 wherein the vaporization is carried out with a fatty alcohol distillation product having a boiling point at 760 mm. Hg in the range of 80°C. to 280°C.

8. A process as claimed in claim 1 wherein the vaporization is carried out with a fatty alcohol distillation product having a boiling point at 760 mm. Hg in the range of 145°C. to 250°C., in an amount of 0.002 to 0.01% by weight with reference to the methanol (calculated as 100%).

9. A process as claimed in claim 1 wherein said elevated temperature is from 600° to 700°C and said pressure is from 0.8 to 1.8 atmospheres where a silver catalyst is employed.

10. A process as claimed in claim 1 wherein the amount of said mixture with reference to said methanol is from 0.002 to 0.01% and wherein the amount of alkanol in this mixture is from 100 to 400% by weight based on the weight of said dialkylether.

* * * * *